US012743480B2

(12) United States Patent
Young et al.

(10) Patent No.: US 12,743,480 B2
(45) Date of Patent: Sep. 22, 2026

(54) SYSTEM AND METHODS FOR CLASSIFYING MAGNETIC RESONANCE IMAGING (MRI) IMAGE CHARACTERISTICS

(71) Applicant: Change Healthcare Holdings, LLC, Nashville, TN (US)

(72) Inventors: Ryan Edward Young, Seattle, WA (US); David Dubois, Mirabel (CA); Ian Michael MacPherson, Toronto (CA)

(73) Assignee: Change Healthcare Holdings, LLC, Nashville, TN (US)

(*) Notice: Subject to any disclaimer, the term of this patent is extended or adjusted under 35 U.S.C. 154(b) by 623 days.

(21) Appl. No.: 17/698,050

(22) Filed: Mar. 18, 2022

(65) Prior Publication Data

US 2023/0297646 A1 Sep. 21, 2023

(51) Int. Cl.
*G06K 9/00* (2022.01)
*G01R 33/54* (2006.01)
(Continued)

(52) U.S. Cl.
CPC ........... *G06F 18/21* (2023.01); *G01R 33/543* (2013.01); *G01R 33/5607* (2013.01);
(Continued)

(58) Field of Classification Search
None
See application file for complete search history.

(56) References Cited

U.S. PATENT DOCUMENTS 4,970,457 A * 11/1990 Kaufman ............ G01R 33/583 324/309
5,560,360 A * 10/1996 Filler .............. G01R 33/56341 600/408

(Continued)

FOREIGN PATENT DOCUMENTS

WO WO-2005067982 A2 * 7/2005 .......... A61K 49/124
WO WO-2010085654 A1 * 7/2010 ............. A61P 43/00

(Continued)

OTHER PUBLICATIONS

Vieira de Mello et al., "Deep Learning-based Type Identification of Volumetric MRI Sequences," 2020 25th International Conference on Pattern Recognition (ICPR), Milan, Italy, 2021, pp. 1-8, doi: 10.1109/ICPR48806.2021.9413120. (Year: 2021).*

(Continued)

*Primary Examiner* — Chan S Park

(74) *Attorney, Agent, or Firm* — MARSHALL, GERSTEIN & BORUN LLP

(57) ABSTRACT

A method for classifying magnetic resonance imaging (MRI) pulse sequences includes receiving medical imaging data associated with an MRI scan, determining one or more pulse sequence characteristics for the medical imaging data using a machine learning model, wherein the medical imaging data is provided as an input to the machine learning model and wherein the machine learning model outputs a classification for each of the one or more pulse sequence (Continued)

characteristics, and updating a database containing the medical imaging data to include the one or more pulse sequence characteristics in association with the medical imaging data.

20 Claims, 4 Drawing Sheets

(51) Int. Cl.

| | |
|---|---|
| ***G01R 33/56*** | (2006.01) |
| ***G06F 18/21*** | (2023.01) |
| ***G06N 3/02*** | (2006.01) |
| ***G06N 20/00*** | (2019.01) |
| ***G06T 7/00*** | (2017.01) |
| ***G06V 10/40*** | (2022.01) |
| ***G06V 10/82*** | (2022.01) |
| ***G06V 40/10*** | (2022.01) |
| ***G16H 30/20*** | (2018.01) |
| ***G16H 30/40*** | (2018.01) |
| ***G16H 50/20*** | (2018.01) |
| ***G16H 50/70*** | (2018.01) |

(52) U.S. Cl.

CPC ........... *G01R 33/5608* (2013.01); *G06N 3/02* (2013.01); *G06N 20/00* (2019.01); *G06T 7/0012* (2013.01); *G06V 10/40* (2022.01); *G06V 10/82* (2022.01); *G06V 40/10* (2022.01); *G16H 30/20* (2018.01); *G16H 30/40* (2018.01); *G16H 50/20* (2018.01); *G16H 50/70* (2018.01); *G06F 2218/08* (2023.01); *G06F 2218/12* (2023.01); *G06T 2207/10088* (2013.01); *G06T 2207/30004* (2013.01); *G06V 2201/03* (2022.01)

(56) References Cited

U.S. PATENT DOCUMENTS 5,644,232 A * 7/1997 Smith .................... G01R 33/56 324/308
5,706,813 A * 1/1998 Filler .................... G01R 33/385 324/318
6,023,634 A * 2/2000 Hanawa ................. G01R 33/54 324/309
6,307,368 B1 * 10/2001 Vasanawala ....... G01R 33/5613 324/309
6,501,272 B1 * 12/2002 Haacke .................. G01R 33/54 324/309
7,227,359 B2 * 6/2007 Ma ..................... G01R 33/4828 324/309
8,005,278 B2 * 8/2011 Mahesh ................. G16H 50/20 382/128
8,150,708 B2 * 4/2012 Kotula ................... G06Q 10/06 382/128
8,311,308 B2 * 11/2012 Chen ................... G06F 18/2148 378/42
8,520,924 B2 * 8/2013 Liao ...................... G06T 7/0016 382/128
8,722,420 B2 * 5/2014 Utsumi .................. A61K 49/20 424/9.3
9,292,921 B2 * 3/2016 Chen ..................... G06T 7/0016
9,370,316 B2 * 6/2016 Ewing .................... A61B 5/055
9,523,750 B2 * 12/2016 Senegas ............. G01R 33/5608
9,687,171 B2 * 6/2017 Kitane ............. G01R 33/56316
10,049,451 B2 * 8/2018 Fisher ................... G06T 7/0012
10,061,003 B2 * 8/2018 James .................... A61B 5/055
10,796,181 B2 * 10/2020 Manickam ........... G06V 10/764
11,379,516 B2 * 7/2022 Peng ....................... G06F 16/55
11,380,432 B2 * 7/2022 Glottmann ............ G06T 7/0012
11,382,601 B2 * 7/2022 Lundberg ............. A61B 8/5207
11,446,009 B2 * 9/2022 Hare, II ................ G16H 50/70
11,553,887 B2 * 1/2023 McLaughlin .......... G16H 40/63
11,559,274 B2 * 1/2023 Auvray .................. A61B 6/481
11,727,087 B2 * 8/2023 Muhamedrahimov .. G06N 3/08 382/131
11,852,706 B2 * 12/2023 Madhuranthakam ........................ G01R 33/5602
11,880,962 B2 * 1/2024 Banerjee ............ G01R 33/5608
11,896,407 B2 * 2/2024 Ma ........................... G06N 3/08
12,020,803 B2 * 6/2024 Narayanan ............. G16H 40/20
12,079,208 B2 * 9/2024 Liu .................. G06F 16/24573
2002/0125887 A1 * 9/2002 Wind ..................... G01R 33/54 324/309
2003/0006770 A1 * 1/2003 Smith .................... G01R 33/56 324/309
2005/0165296 A1 * 7/2005 Ma .................. G01R 33/56563 600/410
2006/0204443 A1 * 9/2006 Kobayashi ........... A61K 49/124 600/1
2007/0053840 A1 * 3/2007 Pandey ................ C07D 487/22 424/9.362
2007/0116336 A1 * 5/2007 Mahesh ................. G16H 50/20 382/128
2008/0116889 A1 * 5/2008 Hu ....................... G01R 33/485 324/309
2009/0006131 A1 * 1/2009 Unger .................... G16H 50/20 705/3
2010/0182008 A1 * 7/2010 Tan .................... G01R 33/5611 324/309
2010/0191099 A1 * 7/2010 Salerno ............. G01R 33/5601 600/420
2010/0211409 A1 * 8/2010 Kotula ................... G16H 50/20 705/2
2010/0264920 A1 * 10/2010 Witschey ........... G01R 33/5605 324/309
2011/0044524 A1 * 2/2011 Wang ................ G01R 33/5601 382/131
2011/0142318 A1 * 6/2011 Chen .................... G06V 10/446 382/131
2012/0134553 A1 * 5/2012 Liao ...................... G06T 7/0016 382/128
2012/0230558 A1 * 9/2012 Chen ..................... G06T 7/0016 382/128
2012/0276644 A1 * 11/2012 Utsumi ............. G01R 33/5601 436/128
2013/0338930 A1 * 12/2013 Senegas ............... G01R 33/546 702/19
2013/0342202 A1 * 12/2013 Mugler, III ...... G01R 33/56509 324/309
2015/0216440 A1 * 8/2015 Senegas ............... A61B 5/7264 600/408
2017/0161894 A1 * 6/2017 Fisher ....................... G06T 7/11
2017/0261584 A1 * 9/2017 James ................ G01R 33/4833
2018/0329006 A1 * 11/2018 Haldar ................. G01R 33/543
2019/0206527 A1 * 7/2019 Boehm .................. A61B 5/055
2019/0269384 A1 * 9/2019 Lundberg ................. A61B 8/08
2019/0303488 A1 * 10/2019 Kubota ................... G06F 16/51
2019/0304577 A1 * 10/2019 Kubota .................. G16H 10/60
2020/0043600 A1 * 2/2020 Glottmann ............. G16H 15/00
2020/0046309 A1 * 2/2020 Auvray .................... A61B 5/33
2020/0089983 A1 * 3/2020 Manickam ............. G06V 10/82
2020/0321100 A1 * 10/2020 Glottmann ............. G06N 3/044
2021/0019342 A1 * 1/2021 Peng ................... G06F 16/5854
2021/0027436 A1 * 1/2021 Banerjee ............... G06T 7/0012
2021/0052252 A1 * 2/2021 Hare, II .................... G06T 7/11
2021/0055364 A1 * 2/2021 Madhuranthakam ....................... A61B 5/0036
2021/0057058 A1 * 2/2021 Liu ........................ G16H 15/00
2021/0169332 A1 * 6/2021 Zimmerman ........ A61B 5/0042
2021/0209757 A1 * 7/2021 Min ..................... A61B 5/7475
2021/0265041 A1 * 8/2021 Narayanan ............. G16H 30/20
2021/0279868 A1 * 9/2021 Ma ........................ G06T 7/0012
2021/0319558 A1 * 10/2021 Min .......................... A61B 8/12
2022/0317223 A1 * 10/2022 Zeller .................. G01R 33/561
2022/0318567 A1 * 10/2022 Muhamedrahimov ..................... A61B 6/481
2022/0342017 A1 * 10/2022 Zeller .................. G01R 33/482

(56) References Cited

U.S. PATENT DOCUMENTS

| | | | | |
|---|---|---|---|---|
| 2022/0392065 | A1* | 12/2022 | Min | A61B 8/0883 |
| 2023/0237655 | A1* | 7/2023 | Otani | G16H 50/20 382/128 |
| 2023/0320612 | A1* | 10/2023 | Sneag | A61K 49/1818 600/411 |

FOREIGN PATENT DOCUMENTS

| | | | | |
|---|---|---|---|---|
| WO | WO-2010097094 | A1 * | 9/2010 | G01R 33/5618 |
| WO | WO-2011103182 | A2 * | 8/2011 | G01N 33/586 |
| WO | 2020/026033 | A2 | 2/2020 | |
| WO | WO-2022096544 | A1 * | 5/2022 | G06T 7/11 |

OTHER PUBLICATIONS

Wikipedia, "Convolutional neural network", published on Mar. 5, 2022 (Year: 2022).*

Liang et al., "Magnetic resonance imaging sequence identification using a metadata learning approach." Frontiers in Neuroinformatics 15 (2021): 622951. (Year: 2021).*

Spin echo—Wikipedia (Year: 2022).*

Pui et al., "MR imaging of the brain: comparison of gradient-echo and spin-echo pulse sequences." AJR. American journal of roentgenology 165, No. 4 (1995): 959-962. (Year: 1995).*

WO-2005067982-A2 (machine translation) (Year: 2005).*

WO-2010085654-A1 (machine translation) (Year: 2010).*

WO-2010097094-A1 (machine translation) (Year: 2010).*

WO-2011103182-A2 (machine translation) (Year: 2011).*

WO-2022096544-A1 (machine translation) (Year: 2022).*

Remedios et al., "Classifying magnetic resonance image modalities with convolutional neural networks." In Medical Imaging 2018: Computer-Aided Diagnosis, vol. 10575, pp. 558-563. SPIE, 2018. (Year: 2018).*

Markl et al., "Gradient echo imaging." Journal of Magnetic Resonance Imaging 35, No. 6 (2012): 1274-1289. (Year: 2012).*

Hargreaves, "Rapid gradient-echo imaging." Journal of Magnetic Resonance Imaging 36, No. 6 (2012): 1300-1313. (Year: 2012).*

Jung et al., "Spin echo magnetic resonance imaging." Journal of Magnetic Resonance Imaging 37, No. 4 (2013): 805-817. (Year: 2013).*

Budde et al., "Functional MRI in human subjects with gradient-echo and spin-echo EPI at 9.4 T." Magnetic resonance in medicine 71, No. 1 (2014): 209-218. (Year: 2014).*

Pui et al., "MR imaging of the brain: comparison of gradient-echo and spin-echo pulse sequences." AJR. American journal of roentgenology 165, No. 4 (1995): 959-962. (Year: 1996).*

Wirestam, "Principles behind Magnetic Resonance Imaging (MRI)." In Handbook of Nuclear Medicine and Molecular Imaging for Physicists, pp. 605-639. CRC Press, 2022. (Year: 2022).*

Wikipedia, "Spin echo", published on Mar. 15, 2022 (Year: 2022).*

Castillo et al., "MR images, brain lesions, and deep learning." Applied Sciences 11, No. 4 (2021): 1675. (Year: 2021).*

Ho et al., "A Machine Learning Approach for Classifying Ischemic Stroke Onset Time From Imaging," in IEEE Transactions on Medical Imaging, vol. 38, No. 7, pp. 1666-1676, Jul. 2019, doi: 10.1109/TMI.2019.2901445. (Year: 2019).*

Search Report from GB2207460.3 mailed Nov. 24, 2022.

* cited by examiner

SYSTEM AND METHODS FOR CLASSIFYING MAGNETIC RESONANCE IMAGING (MRI) IMAGE CHARACTERISTICS

BACKGROUND

The present disclosure relates generally to magnetic resonance imaging (MRI) pulse sequences and more specifically to the classification of MRI pulse sequences. MRI pulse sequences are predefined sets of radio wave pulses and/or pulsed field gradients that are applied during an MRI scan to produce medical images. MRI pulse sequences, or simply MRI sequences, are often designed to take advantage of the various physical characteristics of different tissue type. Thus, by applying specific MRI pulse sequences, medical images can be generated that highlight and/or contrast different tissues, pathologies, etc.

The number of MRI pulse sequences used by radiologists today is constantly increasing; however, many current and forthcoming MRI sequences have proprietary names and/or descriptors that may not properly indicate important characteristics of the associated sequence. Pulse sequences for fat suppression are one such example. Inadequate and/or distinct (e.g., non-universal) naming conventions can impose a burden on radiologists, for example, when searching for an MRI series or when building hanging protocols to display an MRI series correctly. One existing solution is rule-based engines built using Digital Imaging and Communications in Medicine (DICOM) metadata, which is a standard for the communication and management of medical imaging data. These rule-based engines often rely on manually-entered metadata (e.g., DICOM tags) to identify MRI scans that were captured using a similar pulse sequence (e.g., by querying a database to identify historical MRI scans captured using a similar pulse sequence as a subject MRI scan). However, rule-based engines are often fragile and can be broken by small changes to the metadata. More importantly, much of the DICOM data that current rule based engines rely on must be entered by hand by technicians, which can be unreliable (e.g., due to human error). Additionally, data management practices can differ between institutions.

SUMMARY

One implementation of the present disclosure is a method for classifying magnetic resonance imaging (MRI) pulse sequences. The method includes receiving medical imaging data associated with an MRI scan, determining one or more pulse sequence characteristics for the medical imaging data using a machine learning model, wherein the medical imaging data is provided as an input to the machine learning model and wherein the machine learning model outputs a classification for each of the one or more pulse sequence characteristics, and updating a database containing the medical imaging data to include the one or more pulse sequence characteristics in association with the medical imaging data.

In some embodiments, the method further includes extracting features from the medical imaging data prior to determining the one or more pulse sequence characteristics.

In some embodiments, the method further includes displaying the medical imaging data and the one or more pulse sequence characteristics via a user interface.

In some embodiments, the method further includes determining a hanging protocol for the medical imaging data based on the one or more pulse sequence characteristics, and the medical imaging data and the one or more pulse sequence characteristics are displayed according to the hanging protocol.

In some embodiments, the method further includes retrieving the medical imaging data and the one or more pulse sequence characteristics from the database responsive to a user request to view the medical imaging data.

In some embodiments, the machine learning model is a convolutional neural network (CNN).

In some embodiments, the medical imaging data is received from one of the database or a medical imaging device.

In some embodiments, the one or more pulse sequence characteristics include at least one of an indication of whether fat suppression is present, an echo type of the MRI scan, an indication of whether fluid is bright, or an indication of whether contrast is present.

In some embodiments, the one or more pulse sequence characteristics are predefined in a classification schema and the classification for each of the one or more pulse sequence characteristics is a binary classification.

In some embodiments, updating the database further includes generating a custom Digital Imaging and Communications in Medicine (DICOM) tag for the medical imaging data based on the pulse sequence classification.

Another implementation of the present disclosure is a system for classifying magnetic resonance imaging (MRI) pulse sequences. The system includes one or more processors, and a memory device having instructions stored thereon that, when executed by the one or more processors, cause the one or more processors to perform operations including receiving, from a database, medical imaging data associated with an MRI scan, determining one or more pulse sequence characteristics for the medical imaging data using a machine learning model, wherein the medical imaging data is provided as an input to the machine learning model and wherein the machine learning model outputs a classification for each of the one or more pulse sequence characteristics, and updating the database containing the medical imaging data to include the one or more pulse sequence characteristics in association with the medical imaging data.

In some embodiments, the operations further include extracting features from the medical imaging data prior to determining the one or more pulse sequence characteristics.

In some embodiments, the operations further include displaying the medical imaging data and the one or more pulse sequence characteristics via a user interface.

In some embodiments, the operations further include determining a hanging protocol for the medical imaging data based on the one or more pulse sequence characteristics, and the medical imaging data and the one or more pulse sequence characteristics are displayed according to the hanging protocol.

In some embodiments, the operations further include retrieving the medical imaging data and the one or more pulse sequence characteristics from the database responsive to a user request to view the medical imaging data.

In some embodiments, the machine learning model is a convolutional neural network (CNN).

In some embodiments, the one or more pulse sequence characteristics include at least one of an indication of whether fat suppression is present, an echo type of the MRI scan, an indication of whether fluid is bright, or an indication of whether contrast is present.

In some embodiments, the one or more pulse sequence characteristics are predefined in a classification schema and the classification for each of the one or more pulse sequence characteristics is a binary classification.

In some embodiments, updating the database further includes generating a custom Digital Imaging and Communications in Medicine (DICOM) tag for the medical imaging data based on the pulse sequence classification.

Yet another implementation of the present disclosure is a non-transitory computer readable medium having instructions stored thereon that, when executed by one or more processors, cause the one or more processors to perform operations including receiving, from a database, medical imaging data associated with an MRI scan, determining one or more pulse sequence characteristics for the medical imaging data using a neural network, wherein the medical imaging data is provided as an input to the neural network and wherein the neural network outputs a classification for each of the one or more pulse sequence characteristics, and updating a database containing the medical imaging data to include the one or more pulse sequence characteristics in association with the medical imaging data.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Figure 1:
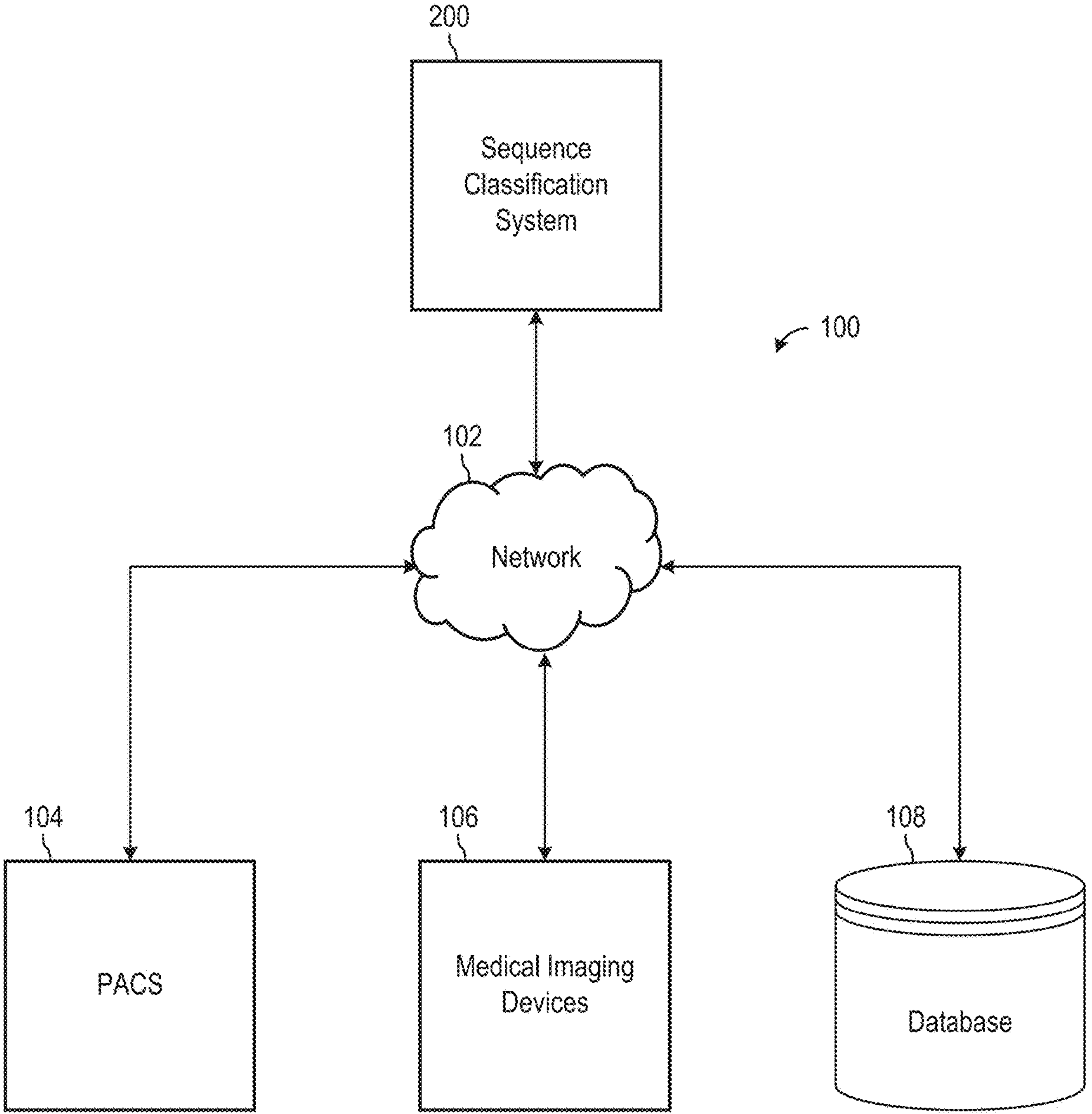
FIG. 1 is a block diagram of a system for processing and classifying medical imaging data, according to some embodiments.

Referring generally to the figures, a system and methods for classifying MRI pulse sequences are shown, accordingly to various embodiments. As noted above, MRI pulse sequences are predefined sets of radio wave pulses and/or pulsed field gradients that are applied during an MRI scan to produce medical images. Specific MRI pulse sequences can be applied during an MRI scan to produce medical images that highlight and/or contrast different tissues, pathologies, etc. In other words, different MRI pulse sequences can be selected based on the type of medical image to be produced and the characteristics of the medical images from an MRI scan may be different between various MRI pulse sequences. Many predefined MRI pulse sequences exist; however, as also discussed above, existing MRI pulse sequences often have proprietary names and/or descriptors that may not properly indicate important characteristics of the associated sequence. This can pose a problem when a user (e.g., a medical professional) attempts to review a study (e.g., medical imaging data from a particular scan) and, more specifically, when the user attempts to access related historical studies for comparison.

As an example, a medical professional reviewing the results of an MRI scan (e.g., a "study") may wish to view other related MRI scans, and their associated data, in parallel. In some cases, related studies may be shown with the subject MRI scan due to predefined "hanging protocols," also referred to as display protocols, which are rules or instructions that determine the images to be displayed and the layout of said images on a picture archiving and communication system (PACS) terminal or other type of workstation. Accordingly, the medical professional and/or the PACS may search for other studies that used a similar MRI pulse sequence as the subject MRI scan. Many current technologies often rely on text-based searches using DICOM tags to identify related studies or images, which can yield undesirable results. For example, many different MRI pulse sequences can exist that provide similar information and MRI manufacturers often create their own unique pulse sequences and variations, which may have unique names, etc. Additionally, MRI pulse sequence data and/or MRI image metadata may often be entered by hand which can introduce human error into naming conventions and tags. Because of this, it can be difficult to locate related studies or MRI images based on pulse sequence name or manually-entered information in DICOM tags.

To address these shortcomings, the system and methods described herein can automatically classify characteristics of an MRI scan by analyzing the MRI image data. The characteristics of the MRI scan can then be utilized to quickly and easily search for related studies (e.g., scans with related characteristics), which may have been captured with a similar pulse sequence due to their shared characteristics. In this manner, a user (e.g., a medical professional) does not need to rely on the manually-entered metadata and/or unique naming conventions of various pulse sequences used in historical MRI scans to locate related studies. In some embodiments, a machine learning model may be applied to MRI image data to extract features and identify various characteristics of the MRI image data. For example, the machine learning model may receive pixel data of the MRI image and may output classifications for various characteristics associated with the MRI image, which in turn can be stored with the MRI image data and/or used to generate a custom DICOM tag for the MRI image data. Thus, the system and methods described herein may avoid human error and variations in pulse sequence naming by automatically classifying characteristics of an MRI pulse sequence using said machine learning model. Additional features and benefits of this system and methods are described in greater detail below.

Turning first to FIG. 1, a block diagram of a system 100 for processing and classifying medical imaging data is shown, according to some embodiments. In particular, system 100 may process MRI image data to determine characteristics of the MRI image data that are indictive of various MRI pulse sequences. Subsequently, system 100 may classify the MRI image data by associating the MRI image data with a known or new pulse sequence. It should be appreciated that, in some embodiments, system 100 includes additional components that are not shown in FIG. 1, but that may be referenced below. Additionally, in some embodiments, system 100 can include fewer components than what is shown in FIG. 1.

As shown, system 100 can include a sequence classification system 200 that handles the processing and classification of MRI image data. In some embodiments, system 200 receives medical imaging data (e.g., MRI image data) from one or both of medical imaging devices 106 and a database 108. As described herein, medical or MRI image data may include both medical images (e.g., MRI scans or pictures) and corresponding metadata (e.g., time of capture, area of the body, etc.). System 200 may process the MRI image data by, in some embodiments, extracting features from the images, and subsequently classifying various characteristics of the MRI image data by applying the MRI image data and/or extracted features to a machine learning model. Based on the classifications of the data's characteristics, database 108 may be updated and/or a DICOM tag may be generated for the MRI image data. Additional details of system 200 are described in greater detail below with respect to FIG. 2.

Medical imaging devices 106, as mentioned above, may include any devices that are capable of capturing medical images. Example medical imaging devices 106 include X-ray machines, computed tomography (CT) scanners, MRI machines, and the like; however, in the implementation shown in FIG. 1, medical imaging devices 106 are generally MRI machines. In some embodiments, system 200 received MRI images (i.e., imaging data) from medical imaging devices 106 via a network 102, as described below. In other embodiments, MRI image data is first stored in database 108 before being retrieved by system 200. Accordingly, database 108 may be hosted on any suitable computing device, such as a server or workstation. In some embodiments, database 108 is hosted on a remote device (e.g., a remote server), or a device that is external to system 200. In other embodiments, database 108 may be hosted on system 200, as described below. In any case, database 108 may be configured to store and maintain MRI image data for later analysis and/or viewing.

In some embodiments, MRI image data is viewed on picture archiving and communication system (PACS) 104. Accordingly, PACS 104 may also be a computing device that is capable of receiving and displaying MRI image data, such as a workstation, a desktop or laptop computer, a smartphone, a tablet, etc. Generally, PACS 104 may allow a user to interact with system 200, and more broadly system 100. In some embodiments, PACS 104 may include a user interface that further includes at least one of a display (e.g., an LCD or LED display) and an input device (e.g., a touchscreen, a mouse, a keypad, etc.). For example, PACS 104 may include a screen that can display MRI images and pulse sequence classifications, as discussed in greater detail below.

Network 102, as mentioned above, is shown to communicably couple system 200, PACS 104, medical imaging devices 106, and database 108. Accordingly, network 102 may be any suitable network that allows for data to be transferred between the components of system 100. In some embodiments, network 102 is a public network, such as the Internet. In other embodiments, network 102 is a private network, such as a virtual private network (VPN). In yet other embodiments, network 102 may include a plurality of public and private connections. For example, network 102 may be a local area network (LAN), a wide area network (WAN), etc. To continue this example, network 102 may be an internal network (e.g., a LAN) for a facility (e.g., a hospital) that allows system 200, PACS 104, medical imaging devices 106, and database 108 to exchange data and/or to access the Internet. It will also be appreciated that, in some embodiments, one or more components of system 100 are remotely connected. For example, PACS 104, medical imaging devices 106, and/or database 108 may be hosted on-site at a facility (e.g., at a hospital) while system 200 may be hosted at a remote site (e.g., on a cloud server).

Figure 2:
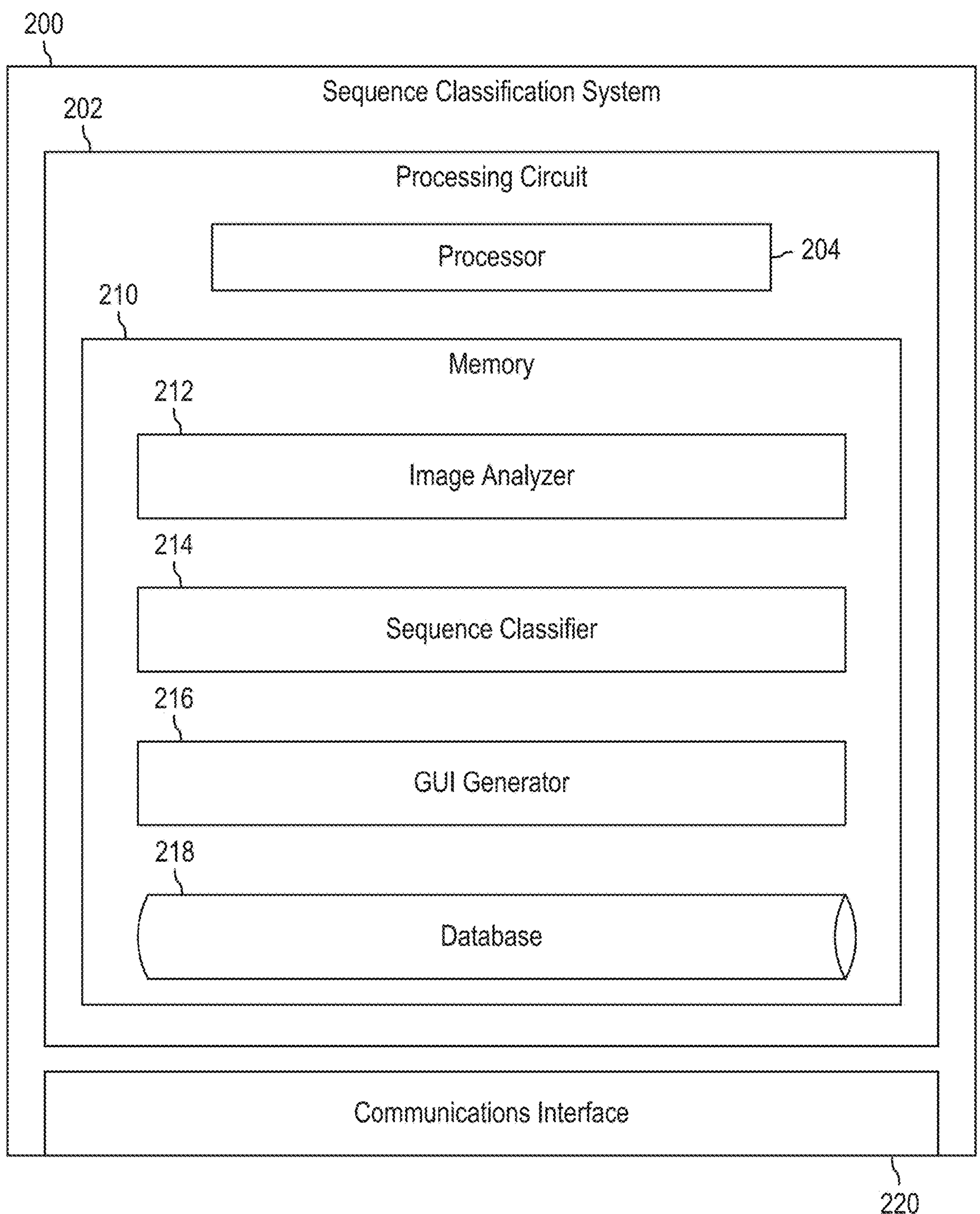
FIG. 2 is a block diagram of an MRI sequence classification system, according to some embodiments.

Referring now to FIG. 2, a detailed block diagram of system 200 is shown, according to some embodiments. Specifically, system 200 is shown to include a processing circuit 202 that further includes a processor 204 and memory 210. Processor 204 can be a general-purpose processor, an application specific integrated circuit (ASIC), one or more field programmable gate arrays (FPGAs), a group of processing components, or other suitable electronic processing components. In some embodiments, processor 204 is configured to execute program code stored on memory 210 to cause system 200 to perform one or more operations. Memory 210 can include one or more devices (e.g., memory units, memory devices, storage devices, etc.) for storing data and/or computer code for completing and/or facilitating the various processes described in the present disclosure.

In some embodiments, memory 210 includes tangible, computer-readable media that stores code or instructions executable by processor 204. Tangible, computer-readable media refers to any media that is capable of providing data that causes the system 200 (i.e., a machine) to operate in a particular fashion. Example tangible, computer-readable media may include, but is not limited to, volatile media, non-volatile media, removable media and non-removable media implemented in any method or technology for storage of information such as computer readable instructions, data structures, program modules or other data. Accordingly, memory 210 can include random access memory (RAM), read-only memory (ROM), hard drive storage, temporary storage, non-volatile memory, flash memory, optical memory, or any other suitable memory for storing software objects and/or computer instructions. Memory 210 can include database components, object code components, script components, or any other type of information structure for supporting the various activities and information structures described in the present disclosure. Memory 210 can be communicably connected to processor 204, such as via processing circuit 2302, and can include computer code for executing (e.g., by processor 204) one or more processes described herein.

While shown as individual components, it will be appreciated that processor 204 and/or memory 210 can be implemented using a variety of different types and quantities of processors and memory. For example, processor 204 may represent a single processing device or multiple processing devices. Similarly, memory 210 may represent a single memory device or multiple memory devices. Additionally, in some embodiments, system 200 may be implemented within a single computing device (e.g., one server, one housing, etc.). In other embodiments controller 110 may be distributed across multiple servers or computers (e.g., that can exist in distributed locations). For example, system 200 may include multiple distributed computing devices (e.g., multiple processors and/or memory devices) in communication with each other that collaborate to perform operations.

Memory 210 is shown to include an image analyzer 212 configured to receive and preprocess MRI image data. In some embodiments, image analyzer 212 receives or retrieves MRI image data from a database 218. As described herein, database 218 may be configured to store and maintain MRI image data. In some embodiments, database 218 is internal to system 200, as shown. In other embodiments, database 218 is external to system 200. In some such embodiments, database 218 may be the same as, or functionally equivalent to, database 108, described above. In yet other embodiments, database 218 may be distributed across multiple servers or computers (e.g., both system 200 and database 108). In any case, image analyzer 212 may preprocess MRI image data by first converting the MRI image data into a suitable format, if necessary.

In some embodiments, image analyzer 212 preprocesses MRI image data by extracting features from the image data, although it will be appreciated that feature extraction may instead be performed by a sequence classifier 214 of memory 210, as described below. Features, as known to those in the art, are individual measurable characteristics of the MRI image data. In some embodiments, preprocessing the MRI image data include converting the MRI image data to a 2-dimensional (2D), black and white image (e.g., from a 3D image); although it will also be appreciated that MRI image data may initially be captured and stored as a black and white 2D image. In other embodiments, the MRI image data is a 3D image that does not need to be converted to a 2D image. In some embodiments, preprocessing the MRI image data includes smoothing of the image data. In some embodiments, image analyzer 212 may perform a Z-transformation on the MRI image data. In some embodiments, image analyzer 212 may perform a histogram correction and/or stretching of the image data.

Once received and/or preprocessed, sequence classifier 214 may evaluate the MRI image data to determine classifications for one or more pulse sequence characteristics. In some embodiments, for example, sequence classifier 214 may extract features from the image data (e.g., as opposed to image analyzer 212) which are then analyzed using a machine learning model. In other embodiments, sequence classifier 214 analyzes MRI image data directly with the machine learning model. In particular, MRI image data and/or extracted features may be provided as an input to the machine learning model implemented by sequence classifier 214, and the machine learning model may output classifications for one or more pulse sequence characteristics. For example, in some embodiments, the machine learning model may evaluate the pixel data of a 2D MRI image to extract information and determine a classification for a plurality of image characteristics. As described herein, the machine learning model may be a convolutional neural network (CNN) or a transformer model. In other embodiments, where an input to the sequence classifier 214 is time-series data, the machine learning model may be a recurrent neural network (RNN). In yet other embodiments, the machine learning model may be any of a linear regression model, a logistic regression model, a Support Vector Machine (SVM), a K-means clustering model, a classification model, etc., or any combination of machine learning models.

Whether a CNN, RNN, or other, similar type of model, the machine learning model may output a classification (e.g., binary classification), or "answer," for each pulse sequence characteristic in a predefined schema. While numerous pulse sequence characteristics may be classified, in some embodiments, sequence classifier 214 may at least determine whether fat suppression is present (e.g., if fat appears bright or dark), whether fluid appears bright or dark, whether contrast is present, an echo type for a subject MRI scan, or any combination thereof. Other example sequence classifier 214 characteristics include whether chemical shift is present, whether cerebral spinal fluid (CFS) and/or grey matter appear bright or dark, etc. In other words, the machine learning model may output a binary classification (e.g., a 0 or 1) for each characteristic to classify the MRI image data as either having the given characteristic, or not having the given characteristic.

In some embodiments, the machine learning model may first (i.e., prior to analyzing new MRI scans) be trained using a known (i.e., "training") set of data. The training data may include historical MRI image data and known classifications for the historical data. For example, the training data may be a dataset that includes multiple MRI images and their corresponding characteristics. In some embodiments, the training data may also include an indication of a pulse sequence associated with the MRI images and characteristics. In this manner, once the machine learning model is trained, sequence classifier 214 may identify a pulse sequence associated with (e.g., used to capture) a given MRI image by first determining the characteristics of the MRI image (e.g., fat suppression, fluid contrast, etc.) and matching the determined characteristics to similar, known MRI image datasets (e.g., with associated pulse sequence identifiers). Subsequently, the identified pulse sequence and/or characteristics associated with the MRI image may be stored in database 218 (e.g., in association with the MRI image data, such as via a pointer or look-up table) and/or a custom DICOM tag may be generated and stored for the MRI image data. The custom DICOM tag may, for example, assign a pulse sequence identifier (i.e., name) to the image data.

Memory 210 is also shown to include a graphical user interface (GUI) generator 216. GUI generator 216 may be configured to generate and display (e.g., or cause a remote device, such as PACS 104, to display) any number of graphical user interfaces (GUIs). In particular, GUI generator 216 may generate and/or display GUIs that include MRI images (e.g., generated from MRI image data) and/or that include or indicate the pulse sequence characteristics associated with a displayed MRI image. In some embodiments, GUI generator 216 can generate a GUI that is constrained to a hanging protocol, which is a set of rules or instructions that determine the images to be displayed and the layout of said images (e.g., on PACS 104). Accordingly, in some such embodiments, GUI generator 216 may automatically retrieve additional MRI image data from database 218 based on the MRI image data to be displayed. In some embodiments, the additional MRI image data is retrieved based on the pulse sequence characteristics identified by sequence classifier 214. In some embodiments, a GUI is generated and/or additional MRI image data is retrieved responsive to a user request to view a particular MRI image or study. For example, a medical professional may "request" to view an MRI study by logging into PACS 104 and/or selecting the MRI study from PACS 104.

Still referring to FIG. 2, system 200 is also shown to include a communications interface 220. Communications interface 220 may facilitate communications between system 200 and any of the components described above in FIG. 1. For example, communications interface 220 can provide means for transmitting data to, or receiving data from, PACS 104, medical imaging devices 106, and database 108. Accordingly, communications interface 220 can be or can include a wired or wireless communications interface (e.g., jacks, antennas, transmitters, receivers, transceivers, wire terminals, etc.) for conducting data communications. In various embodiments, communications via communications interface 220 may be direct (e.g., local wired or wireless communications) or via a network (e.g., a WAN, the Internet, a cellular network, etc.), such as network 102. For example, communications interface 220 can include a WiFi transceiver for communicating via a wireless communications network. In another example, communications interface 220 may include cellular or mobile phone communications transceivers. In yet another example, communications interface 220 may include a low-power or short-range wireless transceiver (e.g., Bluetooth®).

Figure 3:
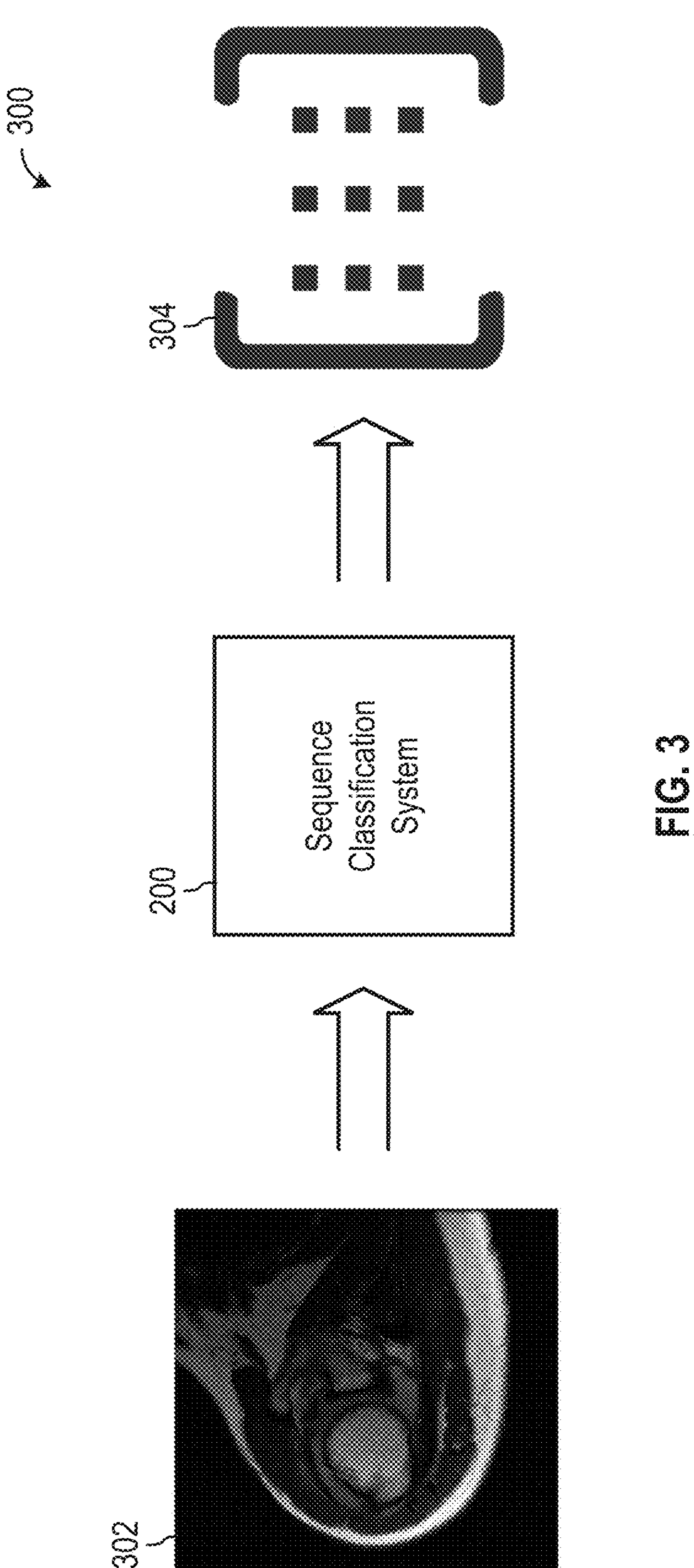
FIG. 3 is a diagram illustrating an example workflow for classifying an MRI sequence based on a captured image, according to some embodiments.

Referring now to FIG. 3, a diagram illustrating an example workflow 300 for classifying an MRI sequence based on a captured image is shown, according to some embodiments. Generally, workflow 300 may represent, at a high level, a process implemented by systems 100, 200, described above. Certain steps of workflow 300 may be described in greater detail below and/or more easily understood with respect to the description of FIG. 4.

Workflow 300 may first begin with the capture of an MRI image 302 (e.g., in this example, an image of a patient's shoulder) by an MRI machine. In some embodiments, MRI image 302 is stored in a database for later retrieval. Subsequently, MRI image 302 is provided or retrieved by system 200 for analysis. In some embodiments, multiple MRI images are retrieved and analyzed by system 200. For example, MRI image 302 may be analyzed (e.g., classified) in real-time or shortly after being captured by an imaging device, or one or more MRI images may be processed in bulk (e.g., continuously or in succession). Thus, workflow 300 may advantageously be implemented on large sets of MRI image data to classify or identify characteristics for each MRI image of the data set, which can make searching a database (e.g., database 218) for pulse sequences and/or MRI images similar to a subject MRI image (e.g., a study being viewed by a user on PACS 104) much simpler than other, existing methods.

As described briefly above, part of the analysis of MRI image 302 by system 200 may include classifying a plurality of pulse sequence characteristics for the image. For example, system 200 may determine, using a machine learning model, whether the pulse sequence used to capture MRI image 302 included fat suppression, whether fluid appears light or dark, etc. Subsequently, these pulse sequence characteristics may be stored in a table 304 or another database element. For example, the pulse sequence characteristics may be stored in a database along with their corresponding MRI images. In this manner, MRI images having similar pulse sequence characteristics, which can indicate that they were captured with similar MRI pulse sequences, may be quickly identified and correlated.

Figure 4:
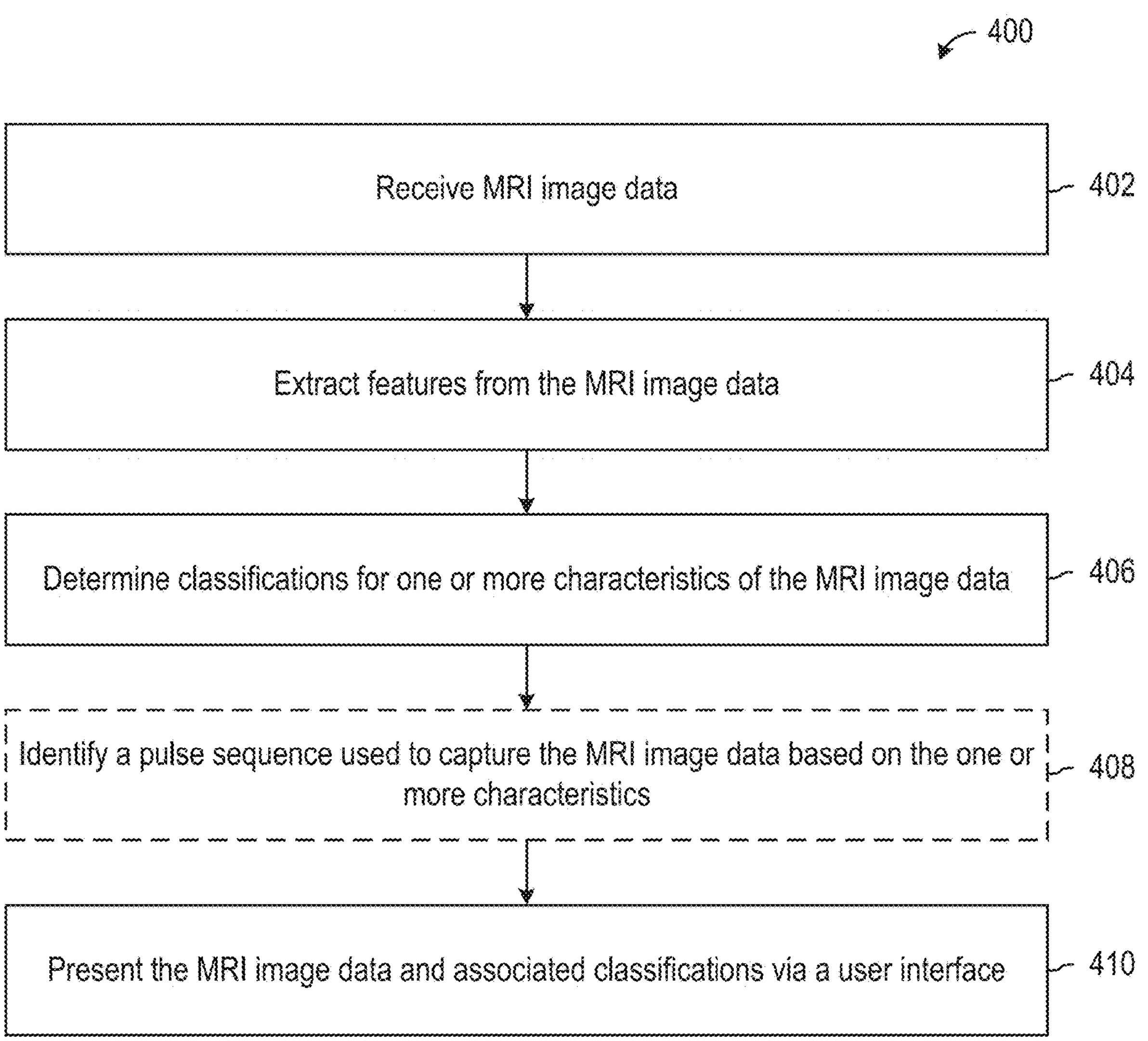
FIG. 4 is a flow diagram of a process for classifying MRI sequences based on medical imaging data, according to some embodiments.

Referring now to FIG. 4, a flow diagram of a process 400 for classifying MRI sequences based on medical imaging data is shown, according to some embodiments. Unlike other methods of classifying MRI image data, which often rely on a user to manually enter identifiers (e.g., pulse sequence names) and characteristics (e.g., which may be inaccurate or non-standard), process 400 advantageously automates the identification and classification of pulse sequence characteristics present in the MRI image data and helps to ensure that MRI images are classified according to a common schema for easy identification. For example, using process 400, important characteristics of an MRI image (e.g., fat suppression, echo type, etc.) can be quickly identified with little to no human input, which reduces error. Identified characteristics for an MRI image can then be used to quickly identify related images (e.g., captured using a similar pulse sequence) without relying on non-standard and/or unique name conventions.

In some cases, process 400 can also be implemented on existing MRI image data sets, such as MRI images that were previously "classified" or associated with a particular pulse sequence. For example, large sets of MRI image data from various institutions, companies, etc., each having a unique naming or identification schema (e.g., unique pulse sequence names), can be analyzed using process 400 to identify the most important characteristics. Thus, a robust data set can be generated that includes many different examples of MRI image data captured using similar pulse sequences, including similar characteristics, etc. In this way, historical MRI images can also be "re-identified" or "reclassified" accordingly to a common schema (e.g., by identifying a core set of image characteristics) to improve searchability and file maintenance. In some embodiments, process 400 is implemented by system 100, as described above. More specifically, in some embodiments, process 400 is implemented at least in part by system 200. It will be appreciated that certain steps of process 400 may be optional and, in some embodiments, process 400 may be implemented using less than all of the steps.

At step 402, MRI image data is received. As described above, the MRI image data may include one or more MRI images (i.e., pictures), typically in the form of a black-and-white, 2D image, and any corresponding metadata. In some embodiments, however, the received MRI image data includes 3D images. In some embodiments, MRI image data is received from one or more medical imaging devices 106 (e.g., MRI machines). In some such embodiments, the MRI image data is subsequently processed (e.g., at steps 404-408 of process 400) in real-time or near real-time. In other such embodiments, the MRI image data is subsequently stored in a database (e.g., database 108 and/or database 218). In some embodiments, rather than being received directly from medical imaging devices 106, the MRI image data is retrieved from a database.

At step 404, features are optionally extracted from the MRI image data. In particular, the MRI image data may be provided as an input to a CNN or other machine learning model that includes at least one feature extraction stage. In a CNN, for example, input image features may be extracted by a feature extraction network, including one or both of convolutional layer(s) and pooling layer(s). The convolutional layer(s) may include a plurality of digital filters for performing a convolution operation on the MRI image data. The pooling layer(s) may dimensionally reduce the input MRI image data and may also set a threshold for feature extraction.

At step 406, classifications for one or more characteristics of the MRI image data are determined. Continuing from step 404 above, for example, the extracted features from the MRI image data may be applied to a classifier network of the CNN for classification. In other embodiments, the MRI image data is simply analyzed by a machine learning model (e.g., a CNN) to determine classifications for one or more pulse sequence characteristics. In either case, the pulse sequence characteristics may indicate various characteristics of the MRI image according to a predefined schema (e.g., of characteristics), such as whether fat suppression is present (e.g., if fat appears bright or dark), whether fluid appears bright or dark, whether contrast is present, an echo type for a subject MRI scan, whether chemical shift is present, whether cerebral spinal fluid (CFS) and/or grey matter appear bright or dark, or any combination thereof.

In some embodiments, the classification of characteristics is binary in that a given MRI image is determined to either include or not include each of the characteristics being classified by the CNN or other machine learning model. In other words, the machine learning model (e.g., CNN) may output a binary classification (e.g., a 0 or 1) for each characteristic to classify the MRI image data as either having the given characteristic, or not having the given characteristic. In some embodiments, the classified characteristics for a given MRI image are stored in a database (e.g., in a table) and are associated with the MRI image in the database. In some embodiments, a custom DICOM tag may be generated that identifies the characteristics for the MRI image.

As mentioned above, properly classifying the characteristics that are present in a given MRI image can be particularly useful for storing, and later retrieving, MRI image data. For example, the MRI image(s) can be stored with tags or other identifiers that indicate the various characteristics associated with the MRI image(s), as classified at step 406. Accordingly, searching for MRI image data in a database (e.g., using PACS 104) becomes less of a chore for a user, as the user can quickly identify a core set of characteristics (e.g., only the most important characteristics) for each data set. As another example, properly classifying the characteristics of MRI image data (e.g., as in step 406) can allow a user to more quickly search a database for historical MRI images or studies that include similar characteristics. In some cases, proper classification can also increase the efficiency with which PACS 104 or another image viewing executes a hanging protocol, which may require identifying historical MRI data having similar characteristics to a subject MRI study (e.g., being viewed on PACS 104).

At step 408, a pulse sequence is optionally identified for the MRI image data based on the characteristics identified in step 406. In some embodiments, the pulse sequence is determined based on previously defined pulse sequences and their associated characteristics. For example, the one or more characteristics of the MRI image data identified at step 406 may be compared to a database of historical MRI images to identify MRI images having similar characteristics. Thus, system 200 can infer that two or more MRI images having similar characteristics were captured using a similar pulse sequence, which may be identified or stored with the historical MRI image data. In this manner, system 200 and/or a user of system 200 may quickly cross-reference a subject MRI image with other, previously-captured MRI images having similar characteristics to identify the MRI pulse sequence used to capture the MRI image. In some embodiments, if a matching MRI image cannot be found for given MRI image data, a new pulse sequence identifier may be generated for the MRI image data. In this manner, any subsequently captured MRI images can be compared to the MRI image data for the new pulse sequence to identify a match. In some embodiments, the identified pulse sequence for a given MRI image is stored in a database (e.g., in a table) and are associated with the MRI image in the database. In some embodiments, a custom DICOM tag may be generated that identifies the pulse sequence.

At step 410, the MRI image data and/or identified image characteristics are presented via a user interface. In particular, PACS 104 may be configured to display the MRI image data and/or characteristics on a user interface responsive to a user request. For example, a physician or other medical professional may access PACS 104 and may retrieve a particular MRI study, which in turn causes system 200 to retrieve the MRI image data and associated (i.e., stored) characteristics (e.g., stored as a DICOM tag, in some case). Subsequently, the MRI image data and/or characteristics may be displayed. In some embodiments, the MRI image data may be stored with a hanging protocol which defines the images to be displayed and/or the layout of the images on the user interface. Accordingly, system 200 may retrieve additional images for display, according to the hanging protocol, such as related MRI images (e.g., to the subject MRI study) captured using a similar pulse sequence.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions, and arrangement of the exemplary embodiments without departing from the scope of the present disclosure.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products including machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor.

When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general-purpose computer, special purpose computer, or special purpose processing machines to perform a certain function or group of functions.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

It is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

What is claimed is:

1. A method for classifying magnetic resonance imaging (MRI) pulse sequences, the method comprising:

receiving, by one or more processors, first medical imaging data associated with an MRI scan;

determining, by the one or more processors, a plurality of pulse sequence characteristics for the first medical imaging data using a machine learning model, wherein the first medical imaging data is provided as an input to the machine learning model, wherein the machine learning model outputs a plurality of binary classifications that includes a binary classification for each characteristic of the plurality of pulse sequence characteristics, and wherein the plurality of pulse sequence characteristics includes at least two of (i) whether fat suppression is present, (ii) an echo type of the MRI scan, (iii) whether fluid is bright, (iv) whether contrast is present, (v) whether chemical shift is present, (vi) whether cerebral spinal fluid (CFS) is bright, or (vii) whether grey matter is bright;

updating, by the one or more processors, a database to include the plurality of binary classifications in association with the first medical imaging data;

generating, by the one or more processors, a pulse sequence identifier for the first medical imaging data, at least in part by:

determining, based on the plurality of binary classifications, whether other medical imaging data in the database has pulse sequence characteristics similar to the plurality of pulse sequence characteristics; and either:

setting the pulse sequence identifier of the first medical imaging data to be a pulse sequence identifier of second medical imaging data in the database when determining, based on the plurality of binary classifications, that the second medical imaging data has pulse sequence characteristics similar to the plurality of pulse sequence characteristics; or generating a new pulse sequence identifier for use as the pulse sequence identifier of the first medical imaging data when determining, based on the plurality of binary classifications, that no other medical imaging data in the database has pulse sequence characteristics similar to the plurality of pulse sequence characteristics; and retrieving, by the one or more processors, responsive to a user request, and based on the plurality of pulse sequence characteristics, third medical imaging data from the database, the third medical imaging data including related MRI scans captured using pulse sequence characteristics similar to the plurality of pulse sequence characteristics.

2. The method of claim 1, further comprising extracting, by the one or more processors, features from the first medical imaging data prior to determining the plurality of pulse sequence characteristics.

3. The method of claim 1, further comprising displaying, by the one or more processors, the first medical imaging data and the plurality of pulse sequence characteristics via a user interface.

4. The method of claim 3, further comprising determining, by the one or more processors, a hanging protocol for the first medical imaging data based on the plurality of binary classifications, wherein the first medical imaging data and the plurality of binary classifications are displayed according to the hanging protocol.

5. The method of claim 3, further comprising retrieving, by the one or more processors, the first medical imaging data and the plurality of binary classifications from the database responsive to a user request to view the first medical imaging data.

6. The method of claim 1, wherein the machine learning model is a convolutional neural network (CNN).

7. The method of claim 1, wherein the first medical imaging data is received from one of the database or a medical imaging device.

8. The method of claim 1, wherein the plurality of binary classifications is predefined in a classification schema.

9. The method of claim 1, wherein updating the database further comprises generating, by the one or more processors, a custom Digital Imaging and Communications in Medicine (DICOM) tag for the first medical imaging data based on the plurality of binary classifications.

10. A system for classifying magnetic resonance imaging (MRI) pulse sequences, the system comprising:

one or more processors; and one or more memories storing processor-executable instructions that, when executed by the one or more processors, cause the one or more processors to perform operations comprising:

receiving first medical imaging data associated with an MRI scan;

determining a plurality of pulse sequence characteristics for the first medical imaging data using a machine learning model, wherein the first medical imaging data is provided as an input to the machine learning model, wherein the machine learning model outputs a plurality of binary classifications that includes a binary classification for each characteristic of the plurality of pulse sequence characteristics, and wherein the plurality of pulse sequence characteristics includes at least two of (i) whether fat suppression is present, (ii) an echo type of the MRI scan, (iii) whether fluid is bright, (iv) whether contrast is present, (v) whether chemical shift is present, (vi) whether cerebral spinal fluid (CFS) is bright, or (vii) whether grey matter is bright;

updating a database to include the plurality of binary classifications in association with the first medical imaging data;

generating a pulse sequence identifier for the first medical imaging data, at least in part by:

determining, based on the plurality of binary classifications, whether other medical imaging data in the database has pulse sequence characteristics similar to the plurality of pulse sequence characteristics; and either:

setting the pulse sequence identifier of the first medical imaging data to be a pulse sequence identifier of second medical imaging data in the database when determining, based on the plurality of binary classifications, that the second medical imaging data has pulse sequence characteristics similar to the plurality of pulse sequence characteristics; or generating a new pulse sequence identifier for use as the pulse sequence identifier of the first medical imaging data when determining, based on the plurality of binary classifications, that no other medical imaging data in the database has pulse sequence characteristics similar to the plurality of pulse sequence characteristics; and retrieving, responsive to a user request, and based on the plurality of pulse sequence characteristics, third medical imaging data from the database, the third medical imaging data including related MRI scans captured using pulse sequence characteristics similar to the plurality of pulse sequence characteristics.

11. The system of claim 10, the operations further comprising extracting features from the first medical imaging data prior to determining the plurality of pulse sequence characteristics.

12. The system of claim 10, the operations further comprising displaying the first medical imaging data and the plurality of pulse sequence characteristics via a user interface.

13. The system of claim 12, the operations further comprising determining a hanging protocol for the first medical imaging data based on the plurality of binary classifications, wherein the first medical imaging data and the plurality of binary classifications are displayed according to the hanging protocol.

14. The system of claim 12, the operations further comprising retrieving the first medical imaging data and the plurality of binary classifications from the database responsive to a user request to view the first medical imaging data.

15. The system of claim 10, wherein the machine learning model is a convolutional neural network (CNN).

16. The system of claim 10, wherein the plurality of binary classifications is predefined in a classification schema.

17. The system of claim 10, wherein updating the database further comprises generating a custom Digital Imaging and Communications in Medicine (DICOM) tag for the first medical imaging data based on the plurality of binary classifications.

18. One or more non-transitory computer readable media storing processor-executable instructions that, when executed by one or more processors, cause the one or more processors to perform operations comprising:

receiving first medical imaging data associated with an MRI scan;

determining a plurality of pulse sequence characteristics for the first medical imaging data using a machine learning model, wherein the first medical imaging data is provided as an input to the machine learning model, wherein the machine learning model outputs a plurality of binary classifications that includes a binary classification for each characteristic of the plurality of pulse sequence characteristics, and wherein the plurality of pulse sequence characteristics includes at least two of (i) whether fat suppression is present, (ii) an echo type of the MRI scan, (iii) whether fluid is bright, (iv) whether contrast is present, (v) whether chemical shift is present, (vi) whether cerebral spinal fluid (CFS) is bright, or (vii) whether grey matter is bright;

updating a database to include the plurality of binary classifications in association with the first medical imaging data;

generating a pulse sequence identifier for the first medical imaging data, at least in part by:

determining, based on the plurality of binary classifications, whether other medical imaging data in the database has pulse sequence characteristics similar to the plurality of pulse sequence characteristics; and either:

setting the pulse sequence identifier of the first medical imaging data to be a pulse sequence identifier of second medical imaging data in the database when determining, based on the plurality of binary classifications, that the second medical imaging data has pulse sequence characteristics similar to the plurality of pulse sequence characteristics; or generating a new pulse sequence identifier for use as the pulse sequence identifier of the first medical imaging data when determining, based on the plurality of binary classifications, that no other medical imaging data in the database has pulse sequence characteristics similar to the plurality of pulse sequence characteristics; and retrieving, responsive to a user request, and based on the plurality of pulse sequence characteristics, third medical imaging data from the database, the third medical imaging data including related MRI scans captured using pulse sequence characteristics similar to the plurality of pulse sequence characteristics.

19. The one or more non-transitory computer readable media of claim 18, wherein the operations further comprise determining a hanging protocol for the first medical imaging data based on the plurality of binary classifications, wherein the first medical imaging data and the plurality of binary classifications are displayed according to the hanging protocol.

20. The one or more non-transitory computer readable media of claim 18, wherein updating the database further comprises generating a custom Digital Imaging and Communications in Medicine (DICOM) tag for the first medical imaging data based on the plurality of binary classifications.

* * * * *